(12) United States Patent  
Bowen et al.

(10) Patent No.: US 8,955,522 B1  
(45) Date of Patent: Feb. 17, 2015

(54) VAPOR DISPENSATION SYSTEM AND REFILL CARTRIDGE

(71) Applicant: Crystal Coast Innovations, LLC, Newport, NC (US)

(72) Inventors: Ronald Bowen, Ayden, NC (US); Corey S. Duber, Ayden, NC (US); Patrick Murphy, Chapel Hill, NC (US); Drew Brisley, Chapel Hill, NC (US)

(73) Assignee: Crystal Coast Innovations, Newport, NC (US)

( * ) Notice: Subject to any disclaimer, the term of this patent is extended or adjusted under 35 U.S.C. 154(b) by 0 days.

(21) Appl. No.: 14/330,061

(22) Filed: Jul. 14, 2014

Related U.S. Application Data

(60) Provisional application No. 62/016,085, filed on Jun. 23, 2014.

(51) Int. Cl.
  *A24F 47/00* (2006.01)
  *A61M 15/06* (2006.01)
  *A61M 15/00* (2006.01)

(52) U.S. Cl.
  CPC .............. *A24F 47/008* (2013.01); *A61M 15/06* (2013.01); *A61M 15/0021* (2014.02)
  USPC ....................... 131/270; 131/273; 128/202.21

(58) Field of Classification Search
  USPC ..................... 131/270, 273, 194; 128/202.21
  See application file for complete search history.

(56) References Cited

U.S. PATENT DOCUMENTS 5,666,977 A * 9/1997 Higgins et al. ................ 131/194
2006/0191546 A1 * 8/2006 Takano et al. ................. 131/270

2009/0151717 A1  6/2009 Bowen et al.
2010/0242974 A1  9/2010 Pan
2011/0277760 A1  11/2011 Terry et al.

FOREIGN PATENT DOCUMENTS

CN    202005248 U   10/2011
CN    202919038 U    5/2013
WO    2013110208 A1  8/2013
WO    2013110209 A1  8/2013

OTHER PUBLICATIONS

Website, screen print provided. http://www.cspnet.com/category-news/tobacco/articles/logic-becomes-pro-vaping, last accessed Nov. 1, 2014.

* cited by examiner

*Primary Examiner* — Richard Crispino
*Assistant Examiner* — Dionne Walls Mayes
(74) *Attorney, Agent, or Firm* — NKK Patent Law, PLLC

(57) ABSTRACT

A vapor dispensation system includes a base having a vaporizing element, a cylindrical vapor tube extending along a longitudinal axis, a mouthpiece connected to the vapor tube opposite the base, a vial body surrounding the vapor tube from the base to the mouthpiece, and a cartridge dimensioned to fit within the vial body. The cartridge has a frangible seal ruptured by the seal penetrating element when the cartridge is enclosed in the vial body between the mouthpiece and base. A method of filling a vapor dispensation system includes disengaging a mouthpiece, removing a spent cartridge, inserting a fluid containing cartridge with a frangible seal of the cartridge oriented toward the vapor dispensation system, rupturing the frangible seal upon full insertion, and engaging the mouthpiece onto the longitudinal end of a vapor dispensation system.

8 Claims, 4 Drawing Sheets

VAPOR DISPENSATION SYSTEM AND REFILL CARTRIDGE

CROSS-REFERENCE TO RELATED APPLICATIONS

This application claims priority to U.S. Provisional Patent Application No. 62/016,085 filed on Jun. 23, 2014, the contents of which are incorporated herein.

TECHNICAL FIELD

The present disclosure relates to vapor dispensation devices. More particularly, the present disclosure relates to a vapor dispensation system refillable by a cartridge having a frangible seal.

BACKGROUND

Electronic cigarettes are increasingly popular. A typical available device includes a vial mounted on a controller. Upon activation of a vaporizing element in the base of the vial, fluid within the vial is vaporized and drifts or is drawn along a vapor tube toward a mouthpiece and dispensed. Once the fluid contents of the vial are depleted, refilling typically occurs by removal of the mouthpiece and direct pouring of concentrated liquid/fluid into the vial. With a typical device, the open top of the vapor tube is vulnerable to contamination during the refilling process. The fluid used in such devices is not intended for consumption as liquid as even in small amounts. Thus such contamination of the vapor tube is unwanted.

Additionally, accidental spills of the concentrated liquid can be very dangerous to a person. Accidental contact with the skin can lead to nausea or worse, and this is particularly problematic if minors can access the concentrated liquid. Incidents of poisoning have been documented.

Improved and convenient refilling devices and methods are needed.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

In at least one embodiment, a vapor dispensation system includes: a base having a vaporizing element; a cylindrical vapor tube connected to the base to receive vapor from the vaporizing element, the vapor tube extending along a longitudinal axis; a mouthpiece connected to the vapor tube opposite the base to receive and dispense vapor from the vapor tube; a vial body surrounding the vapor tube from the base to the mouthpiece, the vial body having an interior seal penetrating element; and a cartridge dimensioned to fit within the vial body, the cartridge having a frangible seal ruptured by the seal penetrating element when the cartridge is enclosed in the vial body between the mouthpiece and base.

In at least one example, the seal penetrating element includes a spike that points along the longitudinal axis away from the base toward the mouthpiece.

In at least one example, the cartridge has an inner cylindrical tube that extends along the longitudinal axis to receive the vapor tube when the cartridge is inserted into the vial body.

In at least one example, the cartridge includes an outer cylindrical wall surrounding the inner cylindrical tube, and annular longitudinal ends.

In at least one embodiment, a method of filling a vapor dispensation system includes: disengaging a mouthpiece from a longitudinal end of a vapor dispensation system; removing a spent cartridge from the longitudinal end of the vapor dispensation system; inserting a fluid containing cartridge into the longitudinal end of the vapor dispensation system with a frangible seal of the cartridge oriented toward the vapor dispensation system; rupturing the frangible seal upon full insertion of the fluid containing cartridge into the vapor dispensation system; and engaging the mouthpiece onto the longitudinal end of a vapor dispensation system.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

DETAILED DESCRIPTIONS

Figure 1:
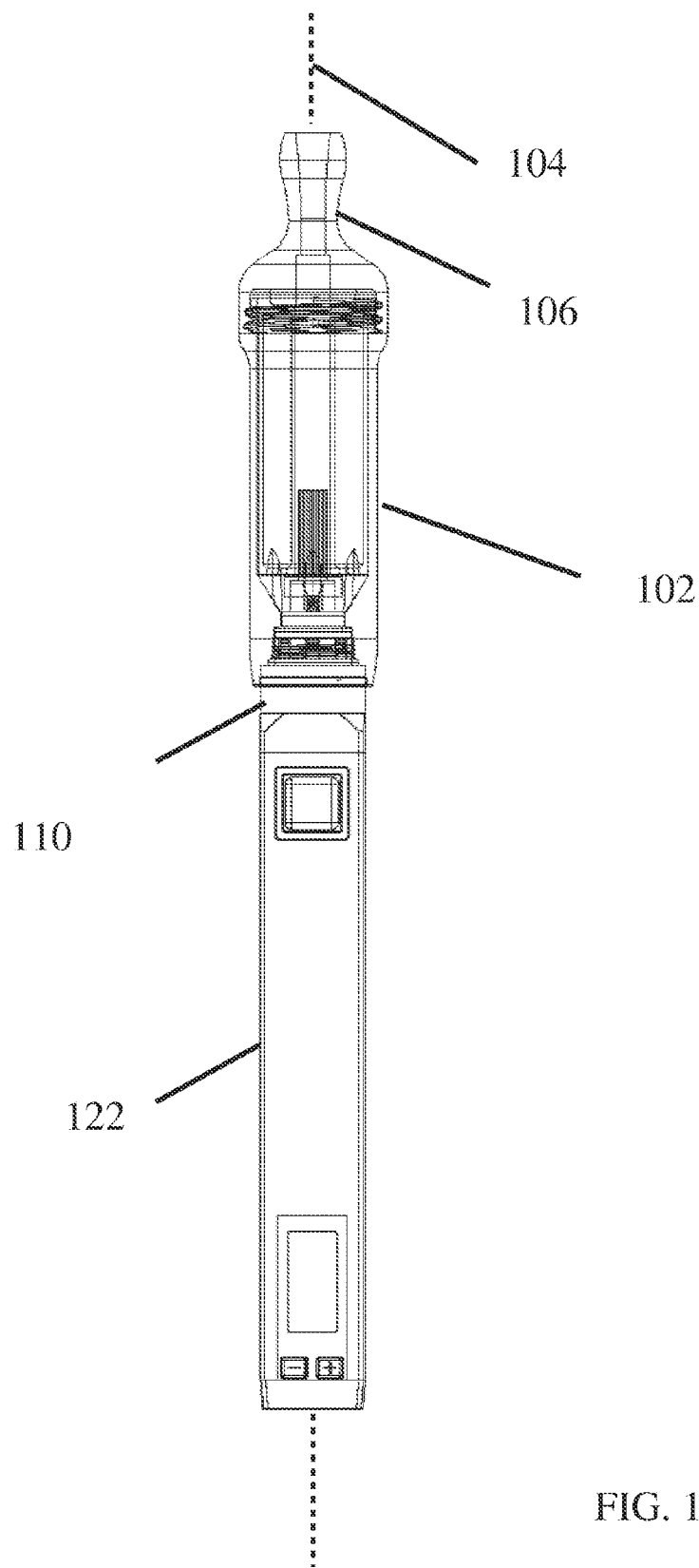
FIG. 1 is an elevation view of a vapor dispensation system having a cartridge loaded reservoir vial according to at least one embodiment.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

FIG. 1 is an elevation view of a vapor dispensation system having a cartridge loaded reservoir vial according to at least one embodiment. The cartridge loaded reservoir vial includes an approximately cylindrical vial body 102 that defines a longitudinal axis 104. A mouthpiece 106 and base 110 define opposing longitudinal ends of the reservoir vial. In FIG. 1, an internal space is defined within the cylindrical vial body 102 between the mouthpiece 106 and base 110. A vapor tube 120 (FIG. 2) extends from the base 110 to the mouthpiece 106. The internal space surrounds the vapor tube 120 and extends from the base 110 to the mouthpiece 106. At the base end of the vial body 102, seal penetrating elements 112 (FIGS. 3-4) extend into the internal space. When the refill cartridge 114 is inserted into the vial body 102, the seal penetrating elements 112 rupture a frangible seal 116 (FIG. 3) of the cartridge 114, making fluid loaded within the cartridge 114 available to a vaporizing element of the base 110.

In one or more embodiments, frangible seal 116 may be removable by peeling away of the seal 116. In this manner, cartridge 114 is installed by orienting the vapor device upside down and inserted the cartridge 114 with the exposed, unsealed end about seal 116 in an upwardly directly.

Figure 2:
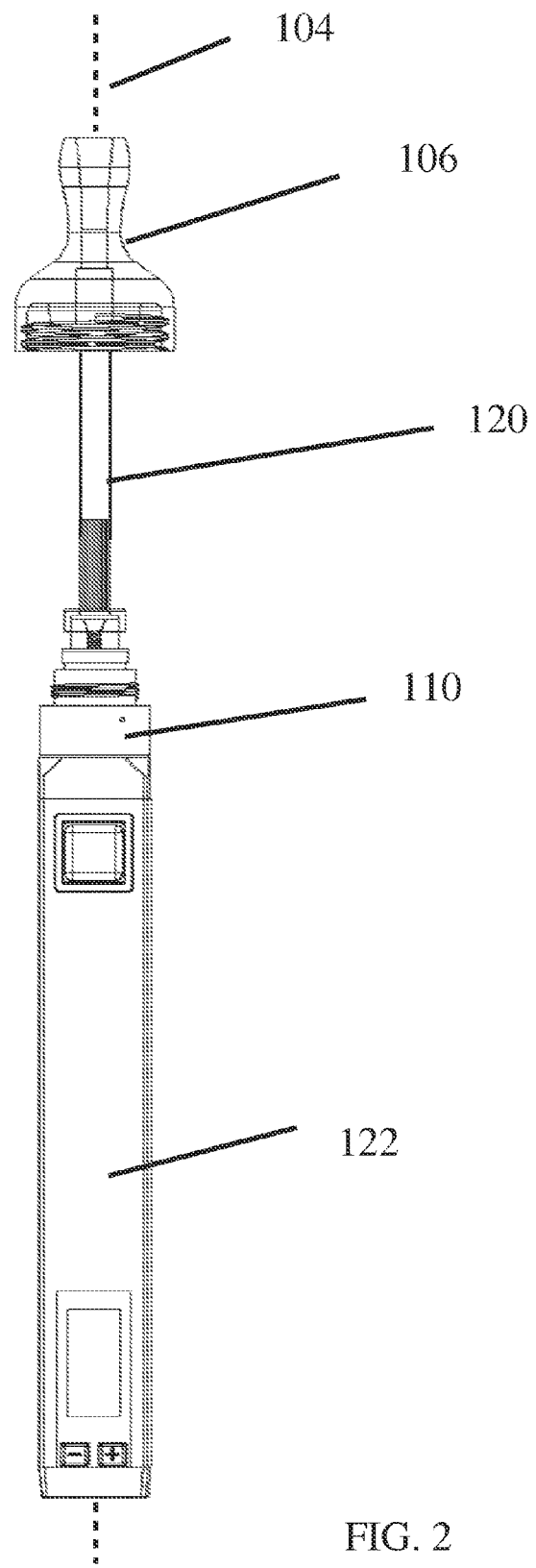
FIG. 2 is an elevation view of core components of the vapor dispensation system of FIG. 1, shown without the cartridge loaded reservoir vial.

FIG. 2 is an elevation view of core components of the vapor dispensation system of FIG. 1, shown without the cartridge loaded reservoir vial. The base 110 is mounted on the upper end of a controller 122 that includes a power source such as batteries. When the controller 122 is activated by use of user accessible buttons, a vaporizing element in the base 110 is energized and vapor is produced. Vapor may be produced by heating, atomizing, or otherwise gasifying a small portion of fluid from within the cartridge 114. The produced vapor drifts or is drawn along the vapor tube 120 from the base 110 to the mouthpiece 106 and is thus dispensed from the mouthpiece.

Figures 3, 4:
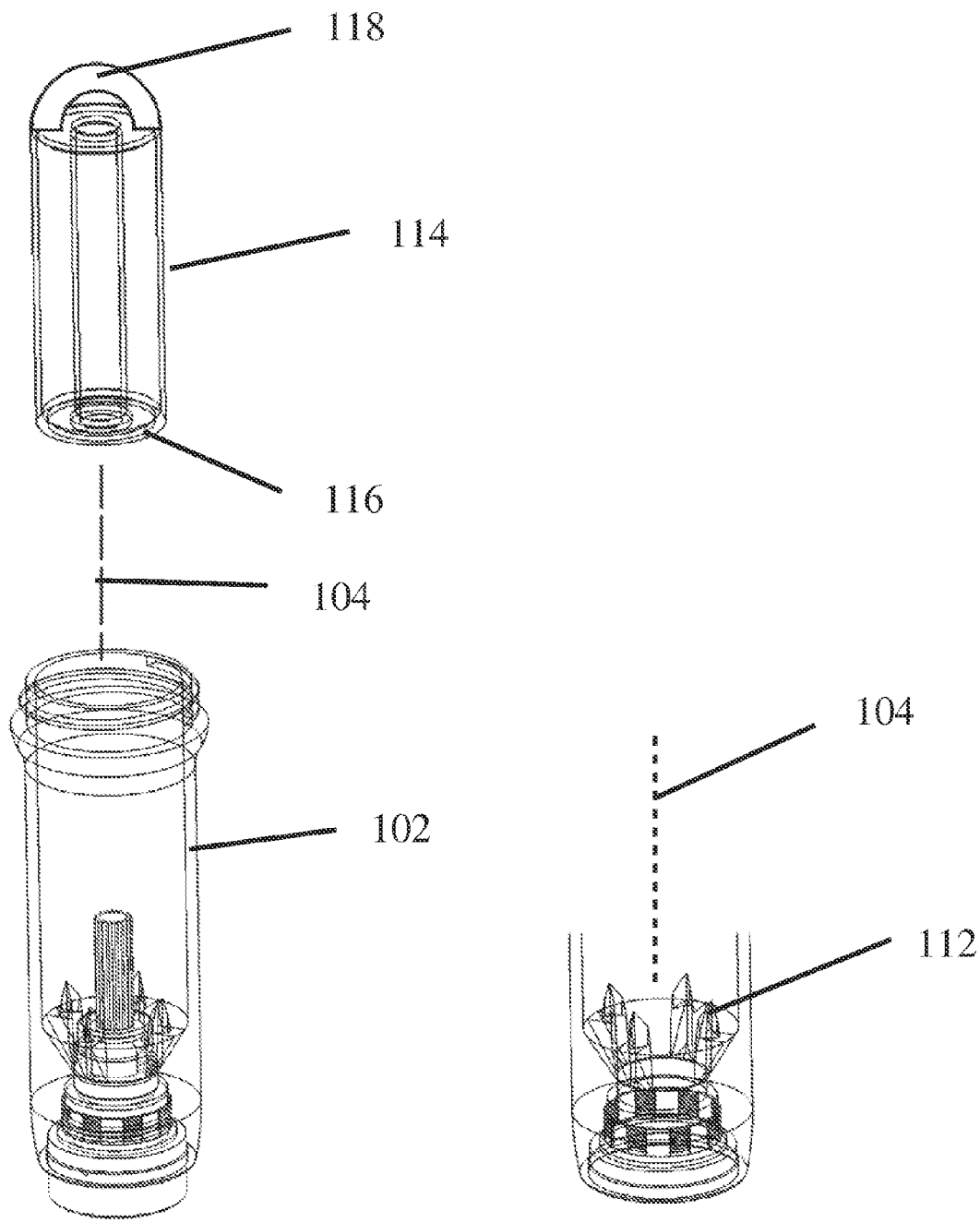
FIG. 3 is an elevation view of the cartridge and reservoir vial of FIG. 1, shown without the core components of FIG. 2.
FIG. 4 is an expanded view of the base end of the reservoir vial, illustrating interior seal penetrating elements.

FIG. 3 shows the vial body 102, having the seal penetrating elements 112 (FIGS. 3-4) that extend into the internal space of the vial body. FIG. 4 is an expanded view of the base end of the reservoir vial, more closely illustrating the seal penetrating elements. The seal penetrating elements 112 are illustrated as spikes pointing from the base end of the vial body 102 toward the mouth piece end of the vial body. The spikes may be integrally formed with the vial body 102 as a ring of spikes surrounding the longitudinal axis 104. Such an example accommodates the illustrated embodiment of the cartridge 114, having the frangible seal 116 formed in its base end as an annular seal.

FIG. 3 also illustrates the refill cartridge 114 as having a cylindrical outer wall and a longitudinal cylindrical inner tube to accommodate the vapor tube 120 (FIG. 2) when the vapor dispensation system (FIG. 1) is assembled. The cartridge 114 has annular longitudinal ends such that a fluid reservoir space is defined between the outer wall, inner tube, and longitudinal ends. The frangible seal 116 is placed at the longitudinal end of the cartridge facing the base 110. The refill cartridge 114, prior to rupturing of the frangible seal 116, contains a fluid sealed within the refill cartridge 114. The frangible seal may be formed of aluminum, aluminized film, foil, and other fluid impermeable but breakable materials. The vial body 102 in at least one embodiment is formed of transparent plastic, acrylic or other clear material permitting visual inspection of its interior as the frangible seal is ruptured and as fluid contents within the cartridge are depleted. The outer wall of the cartridge 114 may also be transparent to permit visual inspection of its contents.

FIG. 3 also illustrates the refill cartridge as having a semi-annular loop 118 by which the cartridge 114 can be manipulated, particularly when the cartridge is to be removed from the vial body 102. The loop 118 can be folded flat against the upper end of the cartridge 114. Like other components of the cartridge, the loop 118 fits, when flattened against the upper end of the cartridge 114, in the annular space between the inner wall of the vial body 102 and the vapor tube 120.

FIG. 2 may represent a core component set of a commercially available device. FIG. 3 represents upgrade components, according to at least one embodiment, by which the component set represented in FIG. 2 can be upgraded to the vapor dispensation system of FIG. 1 having cartridge filling capability.

Figure 5:
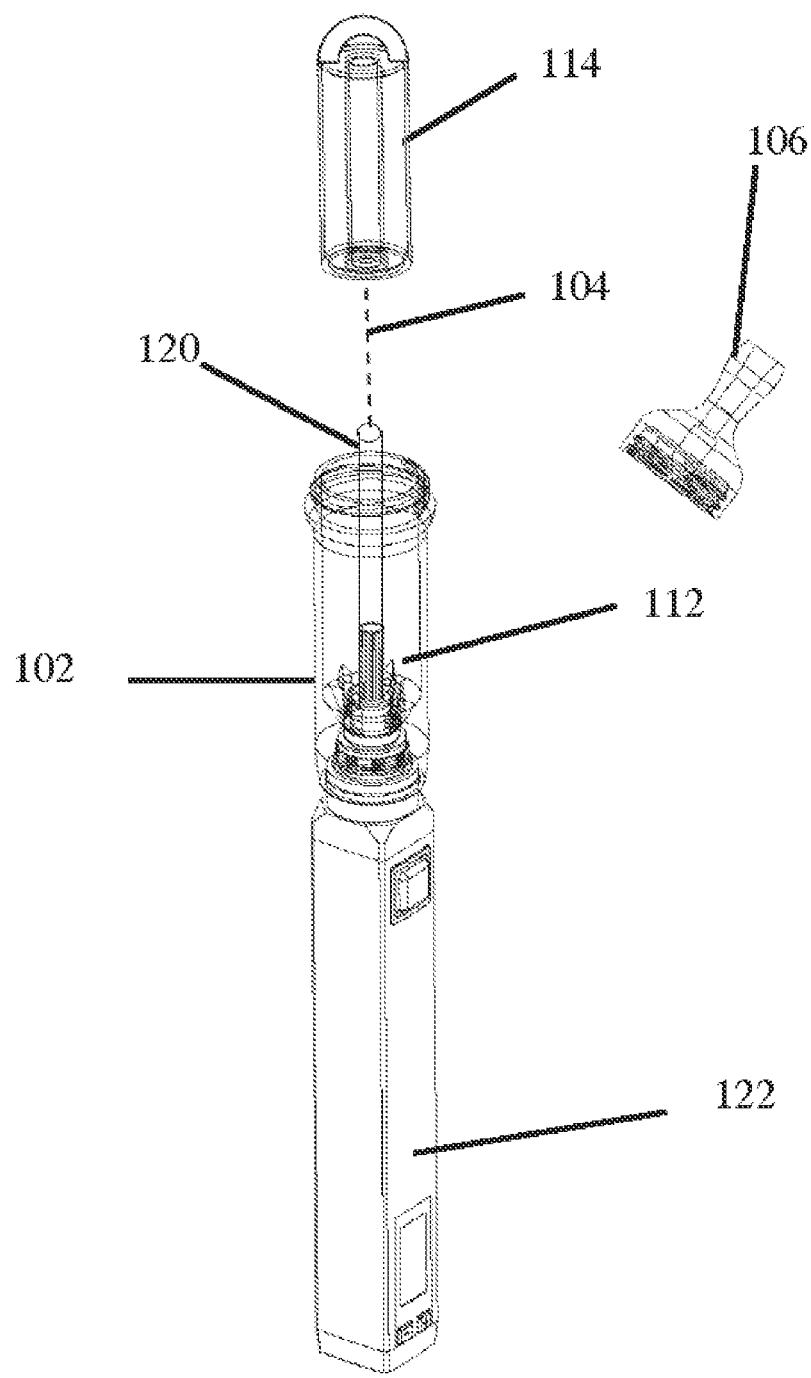
FIG. 5 is a perspective view of the vapor dispensation system of FIG. 1, shown ready for convenient placement of a cartridge into the reservoir vial.

FIG. 5 is a perspective view of the vapor dispensation system of FIG. 1, shown with the mouthpiece 106 removed from the vial body 102, and the refill cartridge 114 with its internal tube aligned with the vapor tub 120 in preparation for loading the cartridge 114 into the internal space of the vial body 102 surrounding the vapor tube. With the cap 114 disengaged (FIG. 5), a cartridge 114 containing a preferred fluid can be loaded into the vial body 102 causing the seal penetrating elements 112 to interrupt the frangible seal 116. The mouth piece can be re-engaged (FIG. 1) to maintain the cartridge 114 in engagement with the base 110. In the illustrated embodiment, the top of the vial body 102 has external threads for engagement with internal threads of the mouth piece 106. In such an embodiment, the mouth piece 106 is disengaged and engaged by rotation by hand.

Advantageously, as shown in FIG. 5, replacement of the cartridge 114 can conveniently occur without disassembly of the vapor dispensation system beyond disengagement of the mouth piece 106 and insertion of the cartridge 114 (followed by engagement of the mouth piece 106). Furthermore, refilling of the vapor dispensation system is conveniently and effectively achieved without risk of fluid inadvertently entering the mouth piece end of the vapor tube 120. When a conventional vapor dispensation system is refilled as prescribed by some manufacturers, fluid is poured directly into a vial body around the open end of the vapor tube and the vapor tube 120 can be unfortunately contaminated. In refilling the vapor dispensation system of FIG. 1 as shown in FIG. 5, the frangible seal 116 at the base end of the cartridge 114 is well below the open top end of the vapor tube 120 before being ruptured. Thus, the open top end of the vapor tube 120 is not exposed to fluid.

One or more methods are thus provided herein. A method of filling a vapor dispensation system includes disengaging a mouthpiece from a longitudinal end of a vapor dispensation system, inserting a fluid containing cartridge into the longitudinal end of the vapor dispensation system with a frangible seal of the cartridge oriented toward the vapor dispensation system, rupturing or removing the frangible seal upon full insertion of the fluid containing cartridge into the vapor dispensation system, and engaging the mouthpiece onto the longitudinal end of the vapor dispensation system.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

What is claimed is:

1. A vapor dispensation system comprising:
 a base having a vaporizing element;
 a cylindrical vapor tube connected to the base to receive vapor from the vaporizing element, the vapor tube extending along a longitudinal axis;
 a mouthpiece connected to the vapor tube opposite the base to receive and dispense vapor from the vapor tube;
 a vial body surrounding the vapor tube from the base to the mouthpiece; and a cartridge dimensioned to fit within the vial body, the cartridge having a frangible seal configured for being either punctured or removed to allow flowthrough of liquid from the cartridge when the cartridge is installed within the vial body.

2. The vapor dispensation system according to claim 1, wherein the vial body has an interiorly placed seal penetrating element and the cartridge has a frangible seal ruptured by the seal penetrating element when the cartridge is enclosed in the vial body between the mouthpiece and base.

3. A vapor dispensation system according to claim 2, wherein the seal penetrating element comprises a spike that points along the longitudinal axis away from the base toward the mouthpiece.

4. A vapor dispensation system according to claim 1, wherein the cartridge has an inner cylindrical tube that extends along the longitudinal axis to receive the vapor tube when the cartridge is inserted into the vial body.

5. A vapor dispensation system according to claim 4, wherein the cartridge comprises an outer cylindrical wall surrounding the inner cylindrical tube, and annular longitudinal ends.

6. The vapor dispensation system according to claim 1, wherein the frangible seal is removed by peeling the seal away from the cartridge.

7. A method of filling a vapor dispensation system of the type having a base having a vaporizing element; a cylindrical vapor tube connected to the base to receive vapor from the vaporizing element, the vapor tube extending along a longitudinal axis; a mouthpiece engaging the vapor tube opposite the base to receive and dispense vapor from the vapor tube; a vial body surrounding the vapor tube from the base to the mouthpiece; and a fluid-containing cartridge dimensioned to fit within the vial body, the cartridge having a frangible seal configured for being either punctured or removed to allow flowthrough of fluid from the cartridge, the method comprising:

disengaging the mouthpiece from the vapor tube;

inserting the cartridge into the vial body with the frangible seal of the cartridge oriented toward the base;

rupturing or removing the frangible seal upon full insertion of the cartridge into the vial body; and engaging the mouthpiece to the vapor tube.

8. The method according to claim 7, further including removing a spent cartridge from the longitudinal end of the vapor dispensation system.

\* \* \* \* \*